United States Patent

Johansson

[11] Patent Number: 5,928,993
[45] Date of Patent: Jul. 27, 1999

[54] AQUEOUS COMPOSITION, AND THE USE OF A WETTING-IMPROVING AGENT

[75] Inventor: Ingegärd Johansson, Göteborg, Sweden

[73] Assignee: Akzo Nobel nv, Arnhem, Netherlands

[21] Appl. No.: 08/930,176

[22] PCT Filed: Apr. 18, 1996

[86] PCT No.: PCT/SE96/00498

§ 371 Date: Oct. 9, 1997

§ 102(e) Date: Oct. 9, 1997

[87] PCT Pub. No.: WO96/34078

PCT Pub. Date: Oct. 31, 1996

[30] Foreign Application Priority Data

Apr. 28, 1995 [SE] Sweden ................... 9501581

[51] Int. Cl.[6] ................ A01N 25/30; C11D 1/66; B01F 17/56
[52] U.S. Cl. ................ 504/116; 514/777; 514/975; 71/DIG. 1; 516/204
[58] Field of Search ................ 252/351; 504/116; 514/777, 975; 71/DIG. 1; 516/204

[56] References Cited

U.S. PATENT DOCUMENTS

| | | | |
|---|---|---|---|
| H303 | 7/1987 | Malik et al. | 514/85 |
| 4,888,325 | 12/1989 | Schroeder et al. | 514/25 |
| 5,258,359 | 11/1993 | Kassebaum et al. | 504/206 |
| 5,663,117 | 9/1997 | Warner | 504/206 |

FOREIGN PATENT DOCUMENTS

| | | | |
|---|---|---|---|
| 0 220 902 | 5/1987 | European Pat. Off. | A01N 57/20 |
| 0 526 443 | 2/1993 | European Pat. Off. | A01N 57/20 |
| WO 88/09369 | 12/1988 | WIPO | C11D 17/00 |
| WO 93/20171 | 10/1993 | WIPO | C11D 1/66 |
| WO 93/22917 | 11/1993 | WIPO | A01N 25/30 |
| WO 94/21655 | 9/1994 | WIPO | C07H 15/04 |
| WO 94/21769 | 9/1994 | WIPO | C11D 1/66 |
| WO 95/04592 | 2/1995 | WIPO | B01F 17/00 |

OTHER PUBLICATIONS

International Search Report, Jul. 18, 1996.

*Primary Examiner*—S. Mark Clardy
*Attorney, Agent, or Firm*—Ralph J. Mancini

[57] ABSTRACT

An aqueous composition which contains a low-foaming alkyl glycoside of the formula (I): $ROG_x$ wherein R is a branched alkyl group having 6–12 carbon atoms, G is a monosaccharide residue, and x is a number in the range of 1–5. When combined with a low-foaming amphoteric compound and/or a low-foaming nonionic alkoxylate, the composition has proved to have a surprisingly good wetting effect. In addition to the surfactant composition, the aqueous composition may contain active substances such as pesticides, herbicides, fertilizers, cleaning surfactants, and alkaline agents.

15 Claims, No Drawings

AQUEOUS COMPOSITION, AND THE USE OF A WETTING-IMPROVING AGENT

This application has been filed under 35 USC 371 on the national stage of international application PCT/SE 96/00498 filed Apr. 18, 1996.

The present invention relates to an aqueous composition which, when applied to a surface, improves the wetting. As wetting-improving agent, the composition contains an alkyl glycoside, which is soluble in the aqueous composition and in which the alkyl group is a branched alkyl chain having 6–12 carbon atoms, in combination with a low-foaming amphoteric compound, which is soluble in the aqueous composition, or a nonionic alkoxylate, which is soluble in the aqueous composition, or a mixture thereof.

Surfactants are generally used for spreading an aqueous composition containing one or more active substances rapidly and evenly over a surface. As a result, the active substances in the composition are put to more efficient use.

Thus, the wetting properties of alkyl polyglycosides are known from Statutory Invention H 303 and U.S. Pat. No. 4,888,325. Further, EP 220 902 proposes that also a foam inhibitor, such as dimethylpolysiloxane, be added to compositions containing alkyl glycoside as wetting agent. Likewise, EP-A-526 443 and WO 93/22917 state that alkyl polyglycosides used as wetting agents may be mixed with respectively an acetylene diol and a fatty alcohol as foam-inhibiting and wetting-improving agent. Since the foam inhibitors proposed have low water solubility, their presence may result in unstable formulations necessitating the addition of a solubiliser. Furthermore, unstable formulations or formulations to which a solubiliser has been added may result in an unacceptably high degree of foaming. Low-molecular solubilisers and foam inhibitors, such as low-molecular alcohols, may also create problems with unpleasant smells.

One object of the present invention is, therefore, to provide a wetting agent of good wetting power not necessitating any extra additions of a foam inhibitor of limited solubility or of a solubiliser.

According to the invention, it has now proved possible to achieve this object and improve the wetting of a surface by using an aqueous composition which, as wetting agent, contains an alkyl glycoside which is soluble in the aqueous composition and has the formula $$ROG_x \qquad (I)$$

wherein R is a branched alkyl group having 6–12 carbon atoms, G is a monosaccharide residue, x is a number in the range of 1–5, and has a foaming not exceeding 25 mm after 5 min at 50° C., as measured according to Ross-Miles, and a concentration of 0.05% by weight, in combination with an amphoteric compound which is soluble in the aqueous composition and contains an alkyl group having 6–12 carbon atoms, and/or a nonionic alkoxylate which is soluble in the aqueous composition and contains an alkyl group having 6–12 carbon atoms, or a mixture thereof, the amphoteric compound and the alkoxylate having a foaming not exceeding 25 mm after 5 min at 50° C., as measured according to Ross-Miles, and a content of 0.05% by weight. The branched alkyl glycosides indicated above have a low tendency towards foaming and result, in combination with the lowfoaming amphoteric or nonionic surfactants indicated above, in excellent wetting properties. The amphoteric surfactant or the nonionic alkoxylate has been found to enhance the wetting power of the alkyl glycoside while keeping foaming at a low level.

The aqueous composition may advantageously be applied e.g. to hydrophobic surfaces, such as those of plant leaves, lacquered metal sheets, plastics, for instance polyethylene or PVC, and glass, as well as surfaces coated with hydrophobic dirt.

The weight ratio of the alkyl glycoside, on the one hand, to the amphoteric compound and/or the alkoxylate, on the other hand, usually ranges from 100:1 to 2:1, preferably from 50:1 to 6:1. In a ready-to-use composition, the total content of all three components may vary within wide limits depending on the field of application, but it normally constitutes 0.1–4% by weight, preferably 0.2–2% by weight. If the composition is in the form of a concentrate that is ready for use after being diluted with water, the content of these three components usually is 2–80% by weight.

The alkyl glycoside of formula I preferably consists of compounds having the general formula

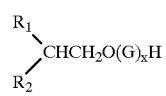

(II)

wherein $R_1$ is an alkyl group having 2–5 carbon atoms, preferably an alkyl group having 2–4 carbon atoms, $R_2$ is an alkyl group having 3–7 carbon atoms, preferably an alkyl group having 4–6 carbon atoms, the sum of carbon atoms in $R_1$ and $R_2$ being 5–12, preferably 6–10, G is a monosaccharide residue, and x is a number in the range of 1–5, preferably 1–4. This alkyl glycoside has good cleaning and wetting properties, as well as low foaming in relation to other straight alkyl glycosides of approximately the same chain length. Especially preferred compounds of formula II are those in which $R_1$ is 3, $R_2$ is 5, and G is a glucose residue. The glucosides have a neutral smell, are easily degraded and have low biotoxicity. In tests, one has not found any skin irritations caused by the alkyl glycosides. SE-A-9300955-3 discloses alkyl glycosides of this type.

Another preferred type of alkyl glycosides are those encompassed by the formula $$R_3CH_2O(G)_xH \qquad (III)$$

wherein $R_3$ is an alkyl group having a total of 6–12 carbon atoms and containing 1–4 groups of the formula —CH (CH$_3$)— forming part of the carbon chain of the alkyl group, G is a monosaccharide residue, and x is a number in the range of 1–5, preferably 1–4. Preferably, the number of methyl groups is 2 or 3. Alkyl glycosides of formula III not only have good cleaning and wetting properties but also exhibit low foaming in relation to glycosides based on straight alcohols having approximately the same chain length. The alkyl glycosides of formula III are easily degraded and have low biotoxicity. In tests, one has not found any skin irritations caused by these alkyl glycosides. Especially preferred compounds are those in which $R_3$ contains 7–11 carbon atoms, since these compounds have a low tendency towards foaming and are relatively easy to produce. SE-A-9300954-6 discloses alkyl glycosides of this type.

Conveniently, the amphoteric surfactant has the general formula

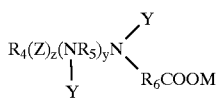 (IV)

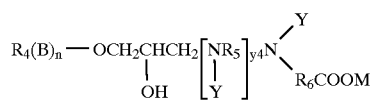 (VIII)

wherein $R_4$ is an alkyl group having 6–12 carbon atoms, Z is the group CO, a group $(B)_n OCH_2CH(OH)CH_2$, in which B is an oxyalkyl group having 2–4 carbon atoms, and n is a number in the range of 0–5, or the group $CH(OH)CH_2$, z is 0 or 1, $R_5$ is the group $—C_2H_4—$ or the group $—C_3H_6—$, y is a group $R_6COOM$, y is a number in the range of 0–3, y being 1–3 when z is 1 and Z is the group CO, $R_6$ is $—CH_2—$ or $—C_2H_4—$, and M is hydrogen or a cation. In addition, the amphoteric compound of formula IV has a surprisingly good solubilising power enabling the preparation of a concentrated aqueous composition.

Amphoteric compounds in which the number of $R_6COOM$ groups is at least 2 are preferred, M preferably being a mono-valent cation, such as an alkali ion or an organic ammonium ion. The designation y preferably is a number in the range of 0–2. The hydrocarbon group $R_4$ preferably is an aliphatic group having 6–15 carbon atoms. Specific examples of suitable $R_4$ groups are hexylt 2-ethylhexyl, capryl and decyl groups, as well as alkyl groups corresponding to those indicated for formulae I, II and III. Examples of suitable amphoteric compounds are compounds having the formulae

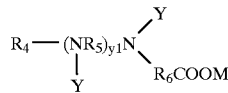 (V)

wherein $R_4$, $R_5$, $R_6$, M and Y have the significations indicated for formula IV, and $y_1$ is a number in the range of 0–2, preferably 0 or 1, the number of $R_6COOM$ groups being at least 2,

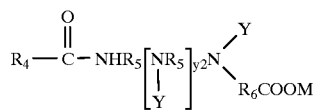 (VI)

wherein $R_4$, $R_5$, $R_6$, Y and M have the significations indicated for formula IV, and $y_2$ is 0 or 1, the number of $R_6COOM$ groups being at least 2,

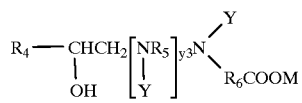 (VII)

wherein $R_4$, $R_5$, $R_6$, Y and M have the significations indicated for formula IV, and $y_3$ is a number in the range of 0–2, preferably 0 or 1, the number of $R_6COOM$ groups being at least 2, and wherein $R_4$, $R_5$, $R_6$, B, Y, M and n have the significations indicated for formula IV, and $y_4$ is a number in the range of 0–2, preferably 0 or 1, the number of $R_6COOM$ groups being at least 2. Preferably, B is an oxyethylene group and n is 0 or 1.

Preferably, the nonionic alkoxylate consists of compounds having the formula $$R_7(C_2H_4O)_x(C_3H_6O)_yH \qquad (IX)$$

wherein $R_7$ is a branched or straight alkyl group having 6–13 carbon atoms, preferably 7–11 carbon atoms, x is a number in the range of 2–6, and y is a number in the range of 0–4, the groups $C_2H_4O$ and $C_3H_6O$ being randomly added or added in blocks. Examples of alkyl groups are groups derived from straight alcohols or branched alcohols, such as oxoalcohols, alcohols having the formula

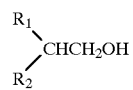 (X)

wherein $R_1$ and $R_2$ have the significations indicated for formula II, and methyl-substituted alcohols having the formula $$R_3CH_2OH \qquad (XI)$$

wherein $R_3$ has the signification indicated for formula III.

In addition to the wetting-agent combination, the aqueous composition applied to a surface contains active substances, such as pesticides, herbicides, fertilisers, cleaning surfactants, and complexing agents, which may be present in solid state or in the form of emulsions, suspensions or solutions. Wetting-agent combinations according to the invention have proved to possess a good stabilising and solubilising power with respect to a great number of active substances. As a result, it has been found easy to formulate stable dispersions, emulsions and solutions having a high content of active substances. The wetting-agent composition is especially suited for use when the formulation consists of solutions and microemulsions having a high content of active substances.

Examples of formulations, in which compositions according to the invention may be used, are micronutrient solutions containing different micronutrients, such as iron, manganese, zinc, copper, boron and molybdenum, which are complexed, preferably to amino carboxylates, such as EDTA, DTPA, MEDTA and EDDHA. Apart from micronutrients, the formulation may advantageously contain macronutrients, such as potassium, nitrogen, phosphorus, magnesium and sulphur.

Other possible formulations are liquid detergents which, besides the alkyl glycoside indicated above, the amphoteric compound and/or the alkoxylate, may contain complexing agents, preferably of amino carboxylate type, such as EDTA, DTPA, HEDTA, NTA and EDDHA, and optionally further surfactants, which may be anionic, nonionic, cationic, amphoteric and/or zwitterionic. For instance, it has been found that the wetting-agent composition according to the invention is especially suited for use in detergents having a high content of alkaline agents, such as alkali hydroxides, complexing agents and silicates, and having a pH value above 11, preferably above 12. The wetting agent according to the invention considerably improves the poor wetting power of these alkaline detergents, which indirectly improves the actual cleaning.

EXAMPLE 1

Test Procedure

A water drop (about 4 ml), which contained different wetting agents and optionally various active substances, such as cleaning surfactants, pesticides, herbicides and fertilisers, was applied to a paraffin-wax surface (Parafilm). The propagation (spreading) of the drop was measured by determining the contact angle after 2 s and 100 s.

The following results were obtained.

| Example | Component | % by weight | Contact angle 2 s | Contact angle 100 s |
|---|---|---|---|---|
| A | 2-ethylhexyl glucoside (x = 1.6) | 1 | 49 | 39 |
| 1 | 2-ethylhexyl glucoside (x = 1.6) | 0.95 | 40 | 29 |
|   | 2-ethylhexyl iminodipropionate (z = 0, y = 0) | 0.05 | | |
| 2 | 2-ethylhexyl glucoside (x = 1.6) | 0.90 | 40 | 30 |
|   | 2-ethylhexyl iminodipropionate (z = 0, y = 0) | 0.1 | | |
| 3 | 2-ethylhexyl glucoside (x = 1.6) | 0.95 | 39 | 30 |
|   | caprylamphopropionate (z = 0, y = 0) | 0.05 | | |
| 4 | 2-ethylhexyl glucoside (x = 1.6) | 0.95 | 34 | 28 |
|   | Undecanol + 3 EO | 0.05 | | |
| 5 | 2-ethylhexyl glucoside (x = 1.6) | 0.95 | 39 | 30 |
|   | 2-hydroxydecyl iminopropionate (z = 0, y = 0) | 0.05 | | |
| 6 | 2-ethylhexyl glucoside (x = 1.6) | 0.95 | 39 | 28 |
|   | 3-octoxy-2-hydroxypropyl iminodiacetate (z = 0, y = 0) | 0.05 | | |
| B | Glyphosate, isopropylamine salt (herbicide) | 0.8 | 97 | 90 |
| C | Glyphosate, isopropylamine salt | 0.8 | 47 | 35 |
|   | 2-ethylhexyl glycoside (x = 1.6) | 1.0 | | |
| 7 | Glyphosate, isopropylamine salt | 0.8 | 38 | 31 |
|   | 2-ethylhexyl glucoside (x = 1.6) | 0.95 | | |
|   | 2-ethylhexyl iminodipropionate (z = 0, y = 0) | 0.05 | | |
| 8 | Glyphosate, isopropylamine salt | 0.8 | 41 | 32 |
|   | 2-ethylhexyl glucoside (x = 1.6) | 0.95 | | |
|   | 3-octoxy-2-hydroxypropyl iminodiacetate (z = 0, y = 0) | 0.05 | | |
| 9 | Glyphosate, isopropylamine salt | 0.8 | 31 | 27 |
|   | 2-ethylhexyl glucoside (x = 1.6) | 0.95 | | |
|   | Undecanol + 3 EO | 0.05 | | |
| D | Leaf fertiliser (NPKS type) | 0.8 | 108 | 105 |
| E | Leaf fertiliser (NPKS type) | 0.8 | 49 | 37 |
|   | 2-ethylhexyl glucoside (x = 1.6) | 0.5 | | |
| 10 | Leaf fertiliser (NPKS type) | 0.8 | 40 | 33 |
|   | 2-ethylhexyl glucoside (x = 1.6) | 0.475 | | |
|   | 2-ethylhexyl iminodipropionate (z = 0, y = 0) | 0.025 | | |
| F | Fertiliser (NKS type) | 0.8 | 90 | 81 |
| H | Fertiliser (NKS type) | 0.8 | 39 | 35 |
|   | 2-ethylhexyl glucoside (x = 1.6) | 0.7 | | |
| 11 | Fertiliser (NKS type) | 0.8 | 36 | 31 |
|   | 2-ethylhexyl glucoside (x = 1.6) | 0.63 | | |
|   | caprylamphopropionate (z = 0, y = 0) | 0.07 | | |
| I | Fertiliser (K type) | 0.8 | 68 | 61 |
| K | Fertiliser (K type) | 0.8 | 40 | 37 |
|   | 2-ethylhexyl glucoside (x = 1.6) | 1.0 | | |
| 12 | Fertiliser (K type) | 0.8 | 35 | 30 |
|   | 2-ethylhexyl glucoside (x = 1.6) | 0.95 | | |
|   | 2-ethylhexyl iminodipropionate (z = 0, y = 0) | 0.05 | | |
| L | 2-propylheptyl glucoside (x = 3.5) | 0.35 | 45 | 31 |
| 13 | 2-propylheptyl glucoside (x = 3.5) | 0.325 | 42 | 29 |
|   | Undecanol + 3 EO | 0.025 | | |
| M | 2-propylheptyl glucoside (x = 3.5) | 0.50 | 35 | 26 |
| 14 | 2-propylheptyl glucoside (x = 3.5) | 0.475 | 33 | 23 |
|   | 3-octoxy-2-hydroxypropyliminodiacetate (z = 0, y = 0) | 0.025 | | |
| 15 | Glyphosate | 0.8 | 31 | 20 |
|   | 2-propylheptyl glucoside (x = 3.5) | 0.475 | | |
|   | 3-octoxy-2-hydroxypropyliminodiacetate (z = 0, y = 0) | 0.025 | | |

It is evident from these results that the spreading with the wetting-agent composition according to the invention is considerably improved, as compared with the case when only low-foaming alkyl glycosides are used.

EXAMPLE 2

The foam height for the following components was measured according to Ross-Miles at a content of 0.05% by weight and at a temperature of 50° C., both at once and after 5 min. The following results were obtained.

| Example | Component | Foam Height, mm 0 min | Foam Height, mm 5 min |
|---|---|---|---|
| 1 | 2-ethylhexyl glucoside (x = 1.6) | 8 | 0 |
| 2 | 2-ethylhexyl iminodipropionate (z = 0, y = 0) | 5 | 0 |
| 3 | caprylamphopropionate (z = 0, y = 0) | 8 | 1 |
| 4 | 1 and 2 in a ratio of 95:5 | 6 | 0 |
| 5 | 1 and 3 in a ratio of 95:5 | 11 | 1 |
| 6 | Undecanol + 3 EO | 15 | 10 |
| 7 | 2-propylhexyl glucoside (x = 3.5) | 22 | 10 |
| 8 | 1 and 6 in a ratio of 95:5 | 25 | 15 |
| 9 | 7 and 6 in a ratio of 93:7 | 23 | 15 |
| 10 | 3-octoxy-2-hydroxypropyl iminodiacetate (z = 0, y = 0) | 36 | 13 |
| 11 | 2-hydroxydecyl iminodipropionate (z = 0, y = 0) | 5 | 0 |
| 12 | 1 and 10 in a ratio of 95:5 | 5 | 0 |
| 13 | 1 and 11 in a ratio of 95:5 | 7 | 0 |
| 14 | 7 and 10 in a ratio of 95:5 | 24 | 11 |
| 15 | 7 and 11 in a ratio of 95:5 | 32 | 16 |
| A | Straight-chained $C_{8-10}$-alkyl glucoside (x = 2) | 60 | 60 |
| B | Straight-chained $C_{8-10}$-alkyl glucoside (x = 2) Straight-chained $C_{8-10}$-alcohol in a ratio of 95:5 | 59 | 56 |

It is evident from these results that the alkyl glycosides according to the invention exhibit much lower foaming than equivalent straight-chained alkyl glycosides. It is especially remarkable that the limited amount of foam formed when use is made of the alkyl glycosides according to the invention collapses fairly rapidly, whereas the alkyl glycoside in the comparative tests A and B gives rise to high-stability foam.

I claim:

1. An aqueous composition which comprises an alkyl glycoside, an amphoteric compound and/or a nonionic alkoxylate, wherein the alkyl glycoside, which is soluble in the aqueous composition, has the formula $$ROG_x \quad (I)$$

wherein R is a branched alkyl group having 6–12 carbon atoms, G is a monosaccharide residue, and x is a number in the range of 1–5, and has a foaming not exceeding 25 mm after 5 min at 50° C., as measured according to Ross-Miles, at a concentration of 0.05% by weight, and that the amphoteric compound and the alkoxylate, which are soluble in the aqueous composition, have an alkyl group containing 6–12 carbon atoms, a foaming not exceeding 25 mm after 5 min at 50° C., as measured according to Ross-Miles, at a content of 0.05% by weight, wherein the weight ratio of the alkyl glycoside to the amphoteric compound and the alkoxylate ranges from 100:1 to 2:1.

2. The composition of claim 1 wherein the alkyl glycoside has the formula

$$\begin{array}{l} R_1 \\ \phantom{R}\diagdown \\ \phantom{RR}CHCH_2O(G)_xH \\ \phantom{R}\diagup \\ R_2 \end{array} \quad (II)$$

wherein $R_1$ is an alkyl group having 2–5 carbon atoms, $R_2$ is an alkyl group having 3–7 carbon atoms, the sum of carbon atoms in $R_1$ and $R_2$ being 5–12, G is a monosaccharide residue, and x is a number in the range of 1–5; or the formula $$R_3CH_2O(G)_xH \quad (III)$$

wherein $R_3$ is an alkyl group having a total of 6–12 carbon atoms and containing 1–4 groups of the formula —CH(CH$_3$)— forming part of the carbon chain of the alkyl group, G is a monosaccharide residue, and x is a number in the range of 1–5, the number of methyl groups being 2 or 3.

3. The composition of claim 2 wherein the sum of carbon atoms in $R_1$ and $R_2$ is 6–10 and x is 1–4.

4. The composition of claim 2 wherein $R_1$ is an alkyl group having 2–4 carbon atoms and $R_2$ is an alkyl group having 4–6 carbon atoms.

5. The composition of claim 1 wherein the amphoteric compound has the formula

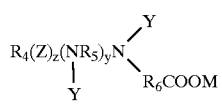

(IV)

wherein $R_4$ is an alkyl group having 6–12 carbon atoms, Z is the group CO, a group $(B)_nOCH_2CH(OH)CH_2$, wherein B is an oxyalkylene group having 2–4 carbon atoms, and n is a number in the range of 0–5, or the group CH(OH)CH$_2$, z is 0 or 1, $R_5$ is the group —C$_2$H$_4$— or the group —C$_3$H$_6$—, Y is a group $R_6$COOM, y is a number in the range of 0–3, y being 1–3 when z is 1 and Z is the group CO, $R_6$ is —CH$_2$— or —C$_2$H$_4$—, and M is hydrogen or a cation.

6. The composition of claim 5 wherein the amphoteric compound has one of the following formulae

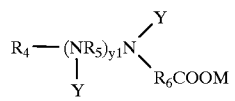

(V)

wherein $R_4$, $R_5$, $R_6$, M and Y have the significations indicated for formula IV, and $y_1$ is a number in the range of 0–2, the number of $R_6$COOM groups being at least 2,

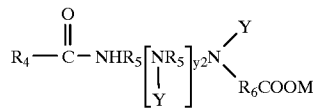

(VI)

wherein $R_4$, $R_5$, $R_6$, Y and M have the significations indicated for formula IV, and $y_2$ is 0 or 1, the number of $R_6$COOM groups being at least 2,

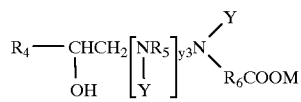

(VII)

wherein $R_4$, $R_5$, $R_6$, Y and M have the significations indicated for formula IV, and $y_3$ is a number in the range of 0–2, the number of $R_6$COOM groups being at least 2, and

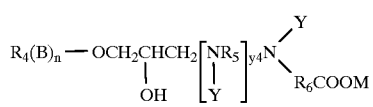

(VIII)

wherein $R_4$, $R_5$, $R_6$, B, Y, M and n have the significations indicated for formula IV, and $y_4$ is a number in the range of 0–2, the number of $R_6$COOM groups being at least 2.

7. The composition of claim 6 wherein $y^4$ is 0 or 1.

8. The composition of claim 6 wherein B is an oxyethylene group and n is 0 or 1.

9. The composition of claim 1 wherein the alkoxylate has the formula $$R_7(C_2H_4O)_x(C_3H_6O)_yH \quad (IX)$$

wherein $R_7$ is a branched or straight alkyl group having 6–13 carbon atoms, x is a number in the range of 2–6, and y is a number in the range of 0–4, the groups $C_2H_4O$ and $C_3H_6O$ being randomly added or added in blocks.

10. The composition of claim 9 wherein the alkoxylate is derived from alcohols of the formula

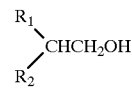

$$\begin{array}{l} R_1 \\ \phantom{R}\diagdown \\ \phantom{RR}CHCH_2OH \\ \phantom{R}\diagup \\ R_2 \end{array} \quad (X)$$

wherein $R_1$ and $R_2$ have the significations indicated for formula II, or from alcohols of the formula $$R_3CH_2OH \quad (XI)$$

wherein $R_3$ is an alkyl group having a total of 6–12 carbon atoms and containing 1–4 groups of the formula —CH(CH$_3$)— forming part of a carbon chain of the alkyl group.

11. The composition of claim 9 wherein $R_7$ is a branched or straight chain alkyl group having 7–11 carbon atoms.

12. The composition of claim 1 which contains a pesticide, a herbicide or a fertilizer.

13. The composition of claim 1 in addition to the alkyl glycoside described above, the amphoteric compound and the alkoxylate, it which additionally contains one or more alkaline agents and optionally further surfactants, which may be anionic, nonionic, cationic, amphoteric and/or zwitterionic.

14. A wetting agent which comprises an alkyl glycoside, an amphoteric compound and/or an alkoxylate as set forth in claim 1.

15. The composition of claim 1 wherein the weight ratio of the alkyl glycoside to the amphoteric compound and the alkoxylate ranges from 50:1 to 6:1.

* * * * *